United States Patent
Toner et al.

(10) Patent No.: US 10,660,776 B2
(45) Date of Patent: May 26, 2020

(54) STENT DELIVERY SYSTEM WITH COLLAPSIBLE LOADING FRAME

(71) Applicant: BOSTON SCIENTIFIC SCIMED, INC., Maple Grove, MN (US)

(72) Inventors: Geraldine A. Toner, Raphoe (IE); Martyn G. Folan, Galway (IE); Enda Connaughton, Galway (IE); Damien V. Nolan, Galway (IE); Matthew Montague, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 117 days.

(21) Appl. No.: 15/483,514

(22) Filed: Apr. 10, 2017

(65) Prior Publication Data
US 2017/0290692 A1 Oct. 12, 2017

Related U.S. Application Data

(60) Provisional application No. 62/321,151, filed on Apr. 11, 2016.

(51) Int. Cl.
*A61F 2/97* (2013.01)
*A61F 2/95* (2013.01)
*A61F 2/966* (2013.01)

(52) U.S. Cl.
CPC ........ *A61F 2/97* (2013.01); *A61F 2002/9528* (2013.01); *A61F 2002/9534* (2013.01); *A61F 2002/9665* (2013.01)

(58) Field of Classification Search
CPC .. A61F 2/962; A61F 2/966; A61F 2/97; A61F 2/95; A61F 2002/9665; A61F 2002/9505; A61F 2002/9511; A61F 2002/9522; A61F 2002/9528; A61F 2002/9534; A61F 2002/9517; A61F 2002/9583; A61F 2002/9586; A61F 2/954; A61F 2/958; A61F 2/2427; A61F 2/243; A61F 2/2433; A61F 2/2436; A61F 2/2434; A61F 2/2439
See application file for complete search history.

(56) References Cited

U.S. PATENT DOCUMENTS 5,026,377 A 6/1991 Burton et al.
5,683,451 A 11/1997 Lenker et al.
(Continued)

FOREIGN PATENT DOCUMENTS

EP 696447 A2 2/1996
WO 2010027485 A2 3/2010

*Primary Examiner* — Katherine H Schwiker
(74) *Attorney, Agent, or Firm* — Seager, Tufte & Wickhem, LLP

(57) ABSTRACT

A stent delivery device including an elongate shaft having a proximal region, a distal region and at least one lumen extending therein. The stent delivery device also includes a collapsible frame attached to the distal region of the elongate shaft. The collapsible frame includes a plurality of arms configured to surround a stent such that the plurality of arms define a stent containment region. The stent delivery device also includes an inner member extending within a least a portion of the stent containment region and an actuation member configured to actuate the plurality of arms of the collapsible frame from an expanded configuration to a collapsed configuration.

17 Claims, 9 Drawing Sheets

(56) References Cited

U.S. PATENT DOCUMENTS

| | | |
|---|---|---|
| 5,800,517 A | 9/1998 | Anderson et al. |
| 5,824,041 A * | 10/1998 | Lenker ............... A61F 2/07 |
| | | 606/195 |
| 6,024,763 A | 2/2000 | Lenker et al. |
| 6,126,685 A | 10/2000 | Lenker et al. |
| 6,132,458 A | 10/2000 | Staehle et al. |
| 6,149,680 A | 11/2000 | Shelso et al. |
| 6,187,016 B1 | 2/2001 | Hedges et al. |
| 6,350,278 B1 | 2/2002 | Lenker et al. |
| 6,355,060 B1 | 3/2002 | Lenker et al. |
| 6,391,050 B1 | 5/2002 | Broome |
| 6,464,683 B1 | 10/2002 | Samuelson et al. |
| 6,514,280 B1 * | 2/2003 | Gilson ............ A61B 17/12031 |
| | | 623/1.11 |
| 6,602,280 B2 | 8/2003 | Chobotov |
| 6,802,846 B2 * | 10/2004 | Hauschild ............ A61B 17/221 |
| | | 606/110 |
| 6,902,575 B2 | 6/2005 | Laakso et al. |
| 6,926,732 B2 | 8/2005 | Derus et al. |
| 7,947,070 B2 | 5/2011 | Headley et al. |
| 3,206,427 A1 | 6/2012 | Ryan et al. |
| 8,317,854 B1 | 11/2012 | Ryan et al. |
| 8,372,132 B2 | 2/2013 | Shin et al. |
| 8,372,133 B2 | 2/2013 | Douk et al. |
| 8,468,667 B2 | 6/2013 | Straubinger et al. |
| 8,652,198 B2 | 2/2014 | Andreas et al. |
| 8,668,728 B2 | 3/2014 | Headley et al. |
| 8,702,780 B2 | 4/2014 | Hartley et al. |
| 8,709,060 B2 | 4/2014 | Osborne |
| 8,998,980 B2 | 4/2015 | Shipley et al. |
| 9,254,371 B2 | 2/2016 | Martin et al. |
| 9,265,639 B2 | 2/2016 | Schneider et al. |
| 9,622,895 B2 | 4/2017 | Cohen et al. |
| 2002/0120277 A1 | 8/2002 | Hauschild et al. |
| 2002/0161377 A1* | 10/2002 | Rabkin ............... A61F 2/95 |
| | | 606/108 |
| 2003/0139795 A1 | 7/2003 | Olson |
| 2004/0064179 A1* | 4/2004 | Linder ............... A61F 2/013 |
| | | 623/1.11 |
| 2006/0184226 A1 | 8/2006 | Austin |
| 2007/0239254 A1* | 10/2007 | Chia ............... A61F 2/2436 |
| | | 623/1.11 |
| 2007/0270932 A1 | 11/2007 | Headley et al. |
| 2008/0015674 A1* | 1/2008 | Austin ............... A61F 2/95 |
| | | 623/1.11 |
| 2009/0082840 A1 | 3/2009 | Rusk et al. |
| 2010/0049313 A1* | 2/2010 | Alon ............... A61F 2/2418 |
| | | 623/2.11 |
| 2010/0331948 A1* | 12/2010 | Turovskiy ............ A61F 2/95 |
| | | 623/1.11 |
| 2011/0082464 A1 | 4/2011 | Douk et al. |
| 2011/0178588 A1 | 7/2011 | Haselby |
| 2011/0190862 A1* | 8/2011 | Bashiri ............... A61F 2/95 |
| | | 623/1.11 |
| 2011/0264191 A1 | 10/2011 | Rothstein |
| 2012/0123515 A1* | 5/2012 | Hosford ............ A61F 2/95 |
| | | 623/1.12 |
| 2012/0172962 A1 | 7/2012 | Nam et al. |
| 2012/0172964 A1 | 7/2012 | Schneider et al. |
| 2013/0110223 A1 | 5/2013 | Munsinger et al. |
| 2013/0123897 A1 | 5/2013 | Robinson |
| 2014/0107758 A1* | 4/2014 | Glazier ............ A61F 2/2436 |
| | | 623/1.12 |
| 2015/0105849 A1 | 4/2015 | Cohen et al. |

\* cited by examiner

STENT DELIVERY SYSTEM WITH COLLAPSIBLE LOADING FRAME

CROSS REFERENCE TO RELATED APPLICATIONS

This application claims the benefit of U.S. Provisional Patent Application Ser. No. 62/321,151 filed on Apr. 11, 2016, the disclosure of which is incorporated herein by reference.

TECHNICAL FIELD

The present disclosure pertains to medical devices, and methods for manufacturing medical devices. More particularly, the present disclosure pertains to elongated intracorporeal medical devices including stent delivery systems, and methods for manufacturing and using such devices.

BACKGROUND

Stents and stent delivery assemblies are utilized in a number of medical procedures and situations, and as such their structure and function are well known. A stent is a generally cylindrical prosthesis that is introduced via a catheter into a body lumen or cavity. The stent is introduced into the body lumen or cavity in a generally reduced diameter (i.e., collapsed) configuration and then expanded to an expanded configuration. In its expanded configuration, the stent supports and reinforces the body lumen or cavity while maintaining the body lumen or cavity in an open, unobstructed condition.

Various medical procedures require placement of large diameter stents within a body lumen or cavity. For example, certain endoscopic procedures may require the use of relatively large diameter stents for placement in the esophagus. Often, a stent is delivered to a target site via a stent delivery system. Some stent delivery systems position the stent between and exterior sheath and an inner support member for delivery to a target site. Loading a stent into this type of stent delivery system often involves sliding an exterior sheath overtop the stent and inner member. With larger stents, this process may result in increased friction forces between the stent and the exterior sheath. Therefore, in some instances it may be desirable to load a stent into a stent delivery system by collapsing a collapsible frame over the stent rather than sliding an exterior sheath overtop. Examples described herein disclose a stent delivery system designed to load a stent by radially collapsing the stent via a collapsible frame, without exposing the stent to longitudinally sliding or shear forces.

BRIEF SUMMARY

This disclosure provides design, material, manufacturing method, and use alternatives for medical devices. An example stent delivery device includes an elongate shaft including a proximal region, a distal region and at least one lumen extending therein. The stent delivery device also includes a collapsible frame attached to the distal region of the elongate shaft, the collapsible frame including a plurality of arms configured to surround a stent such that the plurality of arms define a stent containment region. The stent delivery device also includes an inner member extending within a least a portion of the stent containment region and an actuation member configured to actuate the plurality of arms of the collapsible frame from an expanded configuration to a collapsed configuration.

Alternatively or additionally to any of the embodiments above, wherein the actuation member includes a pull wire.

Alternatively or additionally to any of the embodiments above, wherein the pull wire extends around the plurality of arms in a substantially continuous configuration.

Alternatively or additionally to any of the embodiments above, wherein the collapsible frame further includes at least one aperture defined between one or more of the plurality of arms, wherein the aperture has a width, and wherein the aperture width decreases as the pull wire is actuated.

Alternatively or additionally to any of the embodiments above, wherein each of the plurality of arms includes an opening, and wherein at least a portion of the pull wire extends through the opening of each of the plurality of arms.

Alternatively or additionally to any of the embodiments above, wherein the actuation member includes a tubular member configured to slide over the plurality of arms of the collapsible frame, and wherein the tubular member can shift along a longitudinal axis of the collapsible frame to actuate the plurality of arms of the collapsible frame from the expanded configuration to the collapsed configuration.

Alternatively or additionally to any of the embodiments above, wherein each of the plurality of arms includes a distal portion and a proximal portion, wherein the proximal portion includes a flexible region positioned distal to a distal end of the elongate shaft.

Alternatively or additionally to any of the embodiments above, wherein the flexible region includes a flexible joint configured to maintain a substantially constant distance between the distal portion of the plurality of arms and the elongate shaft.

Alternatively or additionally to any of the embodiments above, further comprising a stent disposed within the stent containment region.

Alternatively or additionally to any of the embodiments above, wherein the stent is positioned between an inner surface of each of the plurality of arms and an outer surface of the inner member.

Alternatively or additionally to any of the embodiments above, wherein the inner surface of each of the plurality of arms defines a concave surface with respect to the outer surface of the inner member, and wherein the concave surface is configured to mate with an outer surface of the stent.

Another example stent delivery system includes:

an elongate shaft including a proximal region, a distal region and at least one lumen extending therein;

a collapsible frame attached to the distal region of the elongate shaft, the collapsible frame including at plurality of arms, the plurality of arms collectively defining a stent containment region; and an actuation member disposed along at least one of the plurality of arms;

wherein the plurality of arms are configured to surround a stent;

wherein the stent containment region has a first diameter corresponding to an expanded configuration and a second diameter corresponding to a collapsed configuration, and wherein actuation of the actuation member is designed to shift the stent containment region from the first diameter to the second diameter.

Alternatively or additionally to any of the embodiments above, further comprising an inner member, wherein the inner member extends through the stent containment region.

Alternatively or additionally to any of the embodiments above, wherein the actuation member includes a pull wire.

Alternatively or additionally to any of the embodiments above, wherein the pull wire extends around the plurality of arms in a substantially continuous configuration.

Alternatively or additionally to any of the embodiments above, wherein each of the plurality of arms includes an opening, and wherein at least a portion of the pull wire extends through the opening of each of the plurality of arms Alternatively or additionally to any of the embodiments above, wherein the actuation member includes a tubular member configured to slide over the collapsible frame, and wherein the tubular member can shift along a longitudinal axis of the collapsible frame to shift the plurality of arms from the first diameter to the second diameter.

Alternatively or additionally to any of the embodiments above, further comprising a stent disposed within the stent containment region.

An example method for loading a stent in a stent delivery device includes:

loading a stent into a stent containment region of a stent delivery device, the stent delivery device including:
an elongate shaft including a proximal region, a distal region and at least one lumen extending therein;
a collapsible frame attached to the distal region of the elongate shaft, the collapsible frame including a plurality of arms configured to surround the stent such that they define the stent containment region;
an inner shaft member extending within a least a portion of the stent containment region; and
an actuation member configured to actuate the plurality of arms of the collapsible frame from an expanded configuration to a collapsed configuration;
actuating the actuation member such that the plurality of arms collapse the stent from an expanded configuration to a collapsed configuration.

Alternatively or additionally to any of the embodiments above, wherein deploying the stent out of the stent containment region further comprises advancing the inner member relative to the collapsible frame to expel the stent out of the stent containment region.

The above summary of some embodiments is not intended to describe each disclosed embodiment or every implementation of the present disclosure. The Figures, and Detailed Description, which follow, more particularly exemplify these embodiments.

BRIEF DESCRIPTION OF DRAWINGS

The disclosure may be more completely understood in consideration of the following detailed description in connection with the accompanying drawings, in which.

Figure 1:
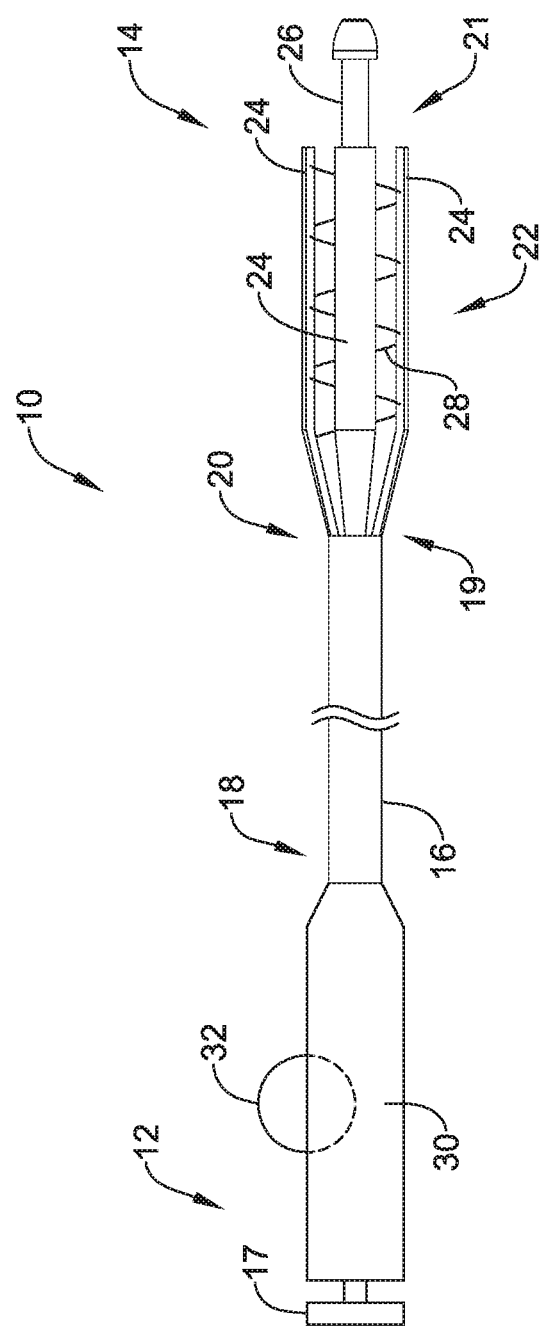
FIG. 1 illustrates an example stent delivery system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Various medical procedures require placement of large diameter stents within a body lumen. For example, certain endoscopic procedures may require the use of relatively large diameter stents for placement in the esophagus. Often, a stent is delivered to a target site via a stent delivery system. Some stent delivery systems position the stent between and exterior sheath and an inner support member for delivery to a target site. Loading a stent into this type of stent delivery system often involves sliding an exterior sheath overtop the stent and inner member. With larger stents, this process may result in increased friction forces between the stent and the exterior sheath. Therefore, in some instances it may be desirable to load a stent into a stent delivery system by collapsing a collapsible frame over the stent rather than sliding an exterior sheath overtop. Examples described herein disclose a stent delivery system designed to radially collapse a stent via a collapsible frame.

FIG. 1 shows an example stent delivery system 10 including a proximal portion 12 and a distal portion 14. Stent delivery system 10 may further include an elongate shaft (e.g., tubular member) 16 having a proximal portion 18 and distal portion 20. Shaft 16 may include one or more lumens extending along at least a portion thereof. In some examples, the one or more lumens of shaft 16 may extend from the distal portion 20 of shaft 16 to the distal portion 20 of shaft 16. In other examples, the one or more lumens of shaft 16 may extend only along a portion of shaft 16.

In some examples, a handle member 30 may be provided along the proximal portion 12 of stent delivery system 10. Further, handle member 30 may be secured to the proximal portion 18 of shaft 16. Handle member 30 may including a grip portion designed to be held by a clinician while manipulating stent delivery system 10 both outside and inside a patient.

In some examples, a collapsible frame 22 may be provided along the distal portion 14 of stent delivery system 10. As shown in FIG. 1, the proximal portion 19 of collapsible frame 22 may be secured to a distal portion 20 of shaft 16. For example, in some instances, collapsible frame 22 may be formed integrally with shaft 16 such that collapsible frame 22 and shaft 16 are a unitary structure, or collapsible frame 22 may be separately formed and attached to shaft 16. Collapsible frame 22 may include one or more, or a plurality of expandable/collapsible arms 24 and an actuation member 28. As illustrated in FIG. 1, each of the collapsible arms 24 may include a proximal end 19 secured to shaft 16 and a distal free end 21. Actuation member 28 may be actuated to radially collapse the collapsible arms 24 from an expanded configuration to a collapsed configuration. In some instances, actuation member 28 may be attached to one or more of the collapsible arms 24, or may be attached to each of the collapsible arms 24, as desired. Additionally, in some examples actuation member 28 may extend within a lumen (not shown) of shaft 16 to handle member 30. Actuation member 28 may extend through a lumen of shaft 16 from a distal portion 20 of shaft 16 to a proximal portion 18 of shaft 16 up to handle member 30.

Further, in some instances actuation member 28 may pass through at least a portion of handle member 30 (via a lumen in handle member 30) and be attached to an actuator 28. In some instances, the actuator 28 may include, for example, a rotatable wheel member, a slider, knob, lever, cam, or other structure. However, it is contemplated that actuator 28 may include other designs.

As shown in FIG. 1, stent delivery system 10 may also include an inner member 26. Inner member 26 may extend coaxially through shaft 16 to handle member 30. In some instances, inner member 26 may be configured to move, shift, translate, slide and/or advance relative to the handle member 30, shaft 16 and/or collapsible frame 22. For example, inner member 26 may be positioned within a lumen of shaft 16. A lumen in which inner member 26 is positioned within shaft 16 may be a second lumen distinct from a lumen in which actuation member 28 is positioned. However, it is contemplated that inner member 26 and actuation member 28 may share a common lumen extending to handle member 39, for example.

Further, inner member 26 may be positioned within a lumen extending within at least a portion of handle member 30. Handle member 30 may include an actuation mechanism 17 configured to longitudinally and/or rotationally actuate inner member 26 relative to shaft 16 and collapsible frame 22. For example, FIG. 1 shows a proximal end of inner member 26 attached to actuation mechanism 17. Actuation mechanism 17 may provide a structure (e.g., grip member) for a clinician to grasp while moving and/or advancing inner member 26 relative to shaft 16 and collapsible frame 22.

Figure 2:
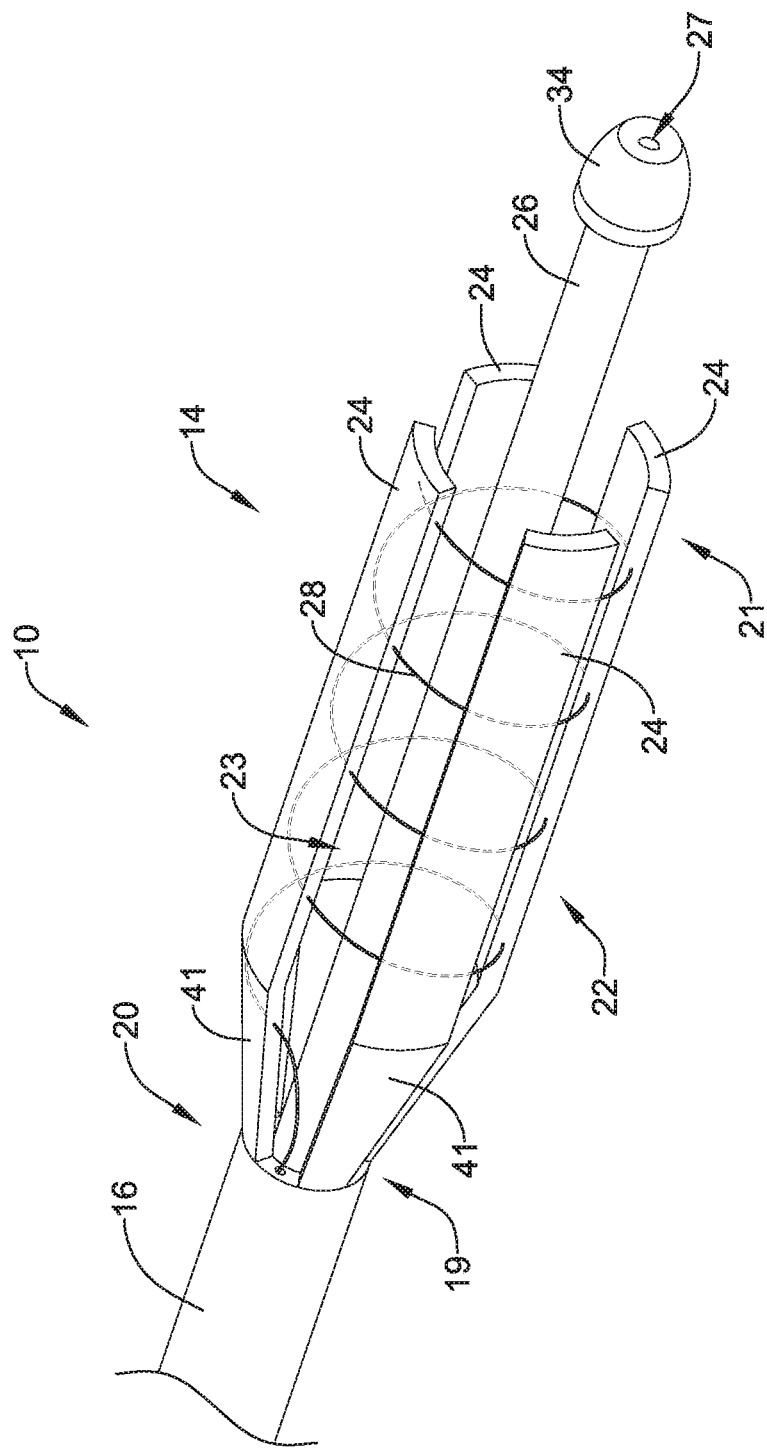
FIG. 2 is a perspective view of the distal end region of the stent delivery system of FIG. 1.

FIG. 2 shows the distal end 14 of stent delivery system 10 including collapsible frame 22, inner member 26 and actuation member 28. FIG. 2 shows collapsible frame including four distinct arms 24. While FIG. 2 shows four arms 24, it is contemplated that collapsible frame 22 may include more or less than four arms 24. For example, example frame 22 may include 2, 3, 4, 5, 6, 7, 8, 9, 10 or more arms 24. Additionally, FIG. 2 shows arms 24 extending from the distal end 21 of collapsible frame 22 to the proximal end 19 of collapsible frame 22.

Arms 24 may be uniformly or non-uniformly arranged around the circumference of collapsible frame 22. As shown in FIG. 2, arms 24 may be spaced apart from each other in an expanded configuration, leaving an opening or gap between adjacent arms 24. In other words, a single arm 24 may extend from the proximal end 19 of collapsible frame 22 to the distal end 21 of collapsible frame 22 without touching another arm 24 along the length of arm 24. Thus, the distal end of each arm 24 may be spaced away from and unattached to the distal end of adjacent arms 24. As shown in FIG. 2, an opening 23 may exist between each of arms 24 in the expanded configuration. Openings 23 may extend from the distal end 20 of shaft 16 to the distal end 21 of collapsible frame 22.

Further, as shown in FIG. 2, one or more of arms 24 may generally have an elongated or rectangular shape. Further, one or more of arms 24 may generally have a curvilinear cross-sectional shape. In other words, with respect to inner member 26, arms 24 may have a concave radially inwardly facing inner surface facing inner member 26 and/or arms 24 may have a convex radially outwardly facing outer surface. Additionally, it can be appreciated from FIG. 2 that arms 24 forming collapsible frame 22, collectively, may resemble a tubular member having a discontinuous outer surface (the discontinuities provided by openings 23). In other words, collectively, the shape of arms 24 may form a generally tubular shape, into which it can be appreciated that a stent, or other similarly shaped medical device, may be inserted therein.

Additionally, arms 24 may include a flexible region 41 at a proximal end of collapsible frame member 22. The flexile region 41 may permit arms 24 to be collapse radially inward from an expanded configuration to a collapsed configuration while arms 24 remain in a longitudinal orientation extending generally parallel with the central longitudinal axis of inner member 26 and/or shaft 16. In other words, flexible region 41 may include a flexible joint that may allow arms 24 to be oriented parallel to the inner member 26 regardless of the size and shape of the stent being loaded into collapsible member 22.

Further, it is contemplated herein that one or more of arms 24 may be replaceable. In other words, flexible joint 41 may be designed such that a portion of one or more of arms 24 may be removed and replaced by an arm 24 having a different configuration (e.g., shape, length, width, thickness, etc.). It can be appreciated that it may be desirable for a clinician to be able to customize the size and/or shape or arms 24 to fit with a particular stent.

As discussed above, actuation member 28 may be configured to actuate collapsible frame 22 from the expanded configuration to the collapsed configuration. For example, actuation member 28 may be attached to one or more of arms 24. FIG. 2 illustrates one example in which actuation member 28 is attached to arms 24. In some examples, the actuation member 28 shown in FIG. 2 may be defined as a pull wire. However, it is contemplated that actuation member 28 may include a variety of materials. For example, actuation member 28 may include a metal (e.g., Nitinol), polymer, textile, or other like materials and combinations thereof.

In some instances, actuation member 28 may be attached to arms 24 in a continuous manner. In other words, actuation member 28 may be a single, unitary member attached to each of arms 24. For example, FIG. 2 shows actuation member 28 exiting the distal end 20 of shaft 16 and forming a substantially continuous helical shape extending around the circumference of collapsible frame 22 to engage each of arms 24. In other instances, actuation member 28 may otherwise by circumferentially disposed around the circumference of collapsible frame 22. Actuation member 28 may extend through an aperture or opening extending through each of arms 24 in some instances. For example, actuation member 28 may be threaded through an opening of each arm 24. In a helical configuration, actuation member 28 may include a plurality of winding around collapsible frame 22. Thus, actuation member 28 may extend through multiple openings through each arm 24 (i.e., one opening for each winding of actuation member 28).

While FIG. 2 shows actuation member 28 being a continuous member being attached through the body of arms 24, it is contemplated that actuation member 28 may include a variety of designs and attachment configurations. For example, it is contemplated that actuation member 28 may be attached to the inner and/or outer surfaces of arms 24. Alternatively, actuation member 28 may surround collapsible frame 22 such that actuation member 28 engages an outer surface of each arm 24 of collapsible frame 22. It is further contemplated that actuation member 28 may be discontinuous. In other words, multiple actuation members 28 (including a variety of materials) may be used to connect and/or attach arms 24 to one another. Additionally, while FIG. 2 shows actuation member 28 forming a generally helical configuration, it is contemplated that actuation member 28 may be arranged in a different configuration when attaching one or more of arms 24 with one another.

As discussed above, inner member 26 is shown extending within collapsible frame 22. In some examples, inner member 26 may be coaxial with the collapsible frame 22 and generally extend in the center of the collection of arms 24 such that the plurality of arms 24 are arranged circumferentially around inner member 26. Further, inner member 26 may include an outer surface designed to aid in the loading of a stent. For example, the outer surface of inner member 26 may include a stent holder which aids in the alignment of the stent and may also assist in constraining the stent when loading and/or deploying the stent out of the collapsible frame 22.

Additionally, inner member 26 may include a distal tip member 34. Distal tip member 34 may be positioned on the distal end of inner member 26. Tip member 34 may have a diameter greater than inner member 26 and may include a proximally-facing surface (perpendicular to the outer surface of inner member 26) which may be designed to be positioned distal of and/or abut the distal end of one or more of arms 24 and/or the distal end of an example stent when a stent is loaded in the stent delivery system 10 in a delivery configuration. Further, FIG. 2 shows that distal tip member 34 includes a guidewire lumen 27 configured to receive a guidewire therethrough. Guidewire lumen 27 may extend within both distal tip member 34 and inner member 26 such that the guidewire lumen 27 extends out of a proximal end of handle member 30, for example.

Figure 3:
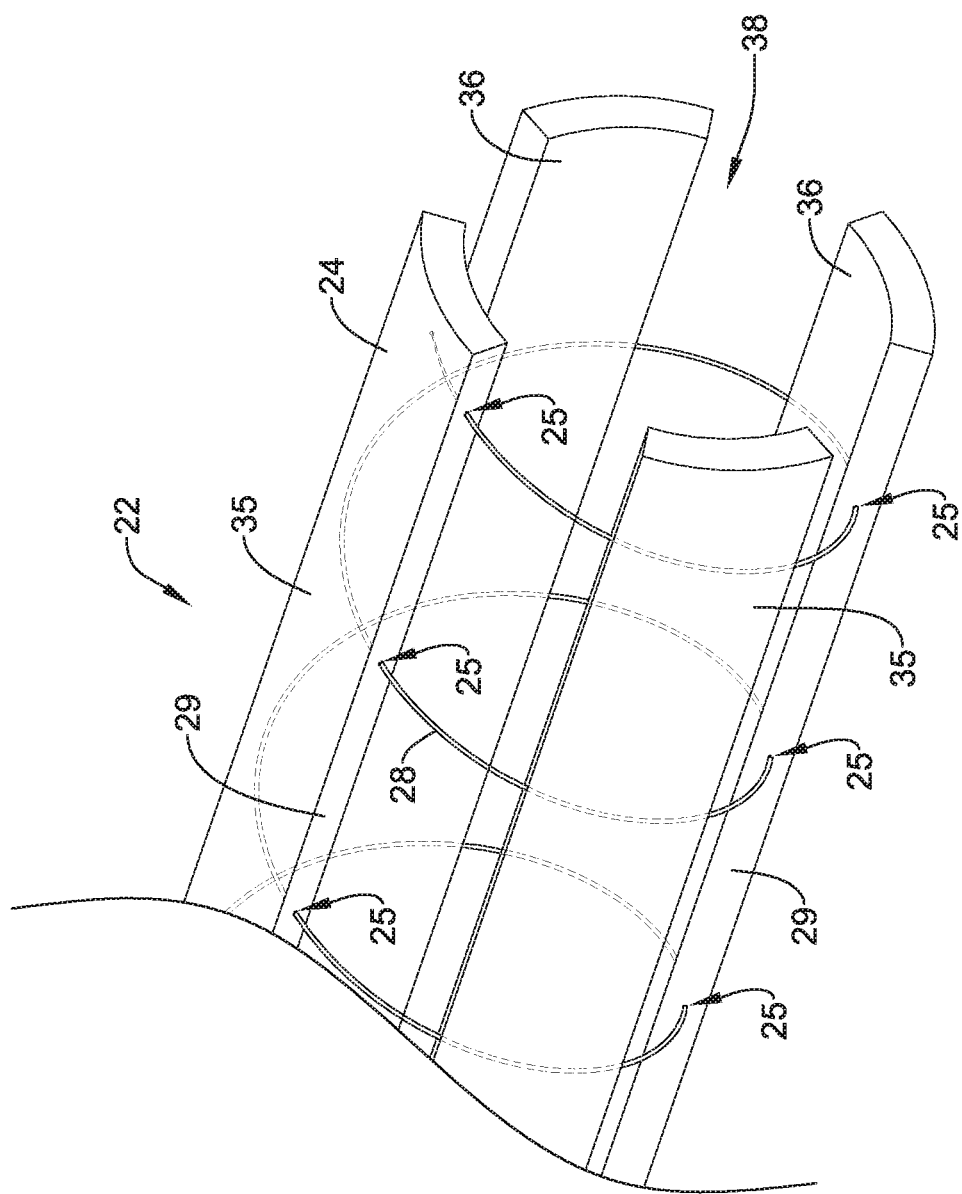
FIG. 3 is an enlarged perspective view of the distal end region of the stent delivery system show in FIG. 2.

FIG. 3 illustrates an example actuation member 28 extending (e.g., being routed) through the body of one or more of arms 24 of collapsible frame 22. The actuation member 28 routed through arms 24 is depicted by the dashed lines shown in FIGS. 2 and 3. In some instances, actuation member 28 may be helically wound around collapsible frame 22, one or more, two or more, three or more, or four or more complete revelations, if desired. As illustrated, actuation member 28 may be inserted or exit into one or more insertion/exit points (e.g., openings) 25 along one or more of arms 24. The actuation member 28 may be channeled through the body of one or more arms 24 before exiting a given arm 24, spanning opening 23 and then re-inserting into another one of arms 24 (e.g., an adjacent arm 24). Actuation member 28 may be able to move relative to (e.g., slide within openings) arms 24. While FIG. 3 shows actuation member 28 entering and exiting side surfaces 29 of arms 24, it is contemplated actuation member 28 may enter and exit the radially outward surface 35, radially inward surface 36, side surface 29 or combinations thereof. In alternative embodiments, actuation member 28 may be threaded through eyelets or loops form with and/or attached to arms 24, for example.

The distal end of actuation member 28 may be secured to one of arms 24. For example, the distal end of actuation member 28 may be secured near a distal end of one or arms 24. In other embodiments, the distal end of actuation member 28 may be secured to shaft 16. In another embodiment, the actuation member 28 may be looped around collapsible frame 22 such that both ends of actuation member 28 are located with the handle member 30, for example.

Additionally, as described above, FIG. 3 shows a radially inward surface 36 of arms 24 including a substantially concave shape. The some examples, the concave surface of inner surface 36 may be designed to generally mate with a convex shape of the outer surface of an example stent member. Likewise, the radially outward surface 35 of arms may include a substantially convex shape. However, other surface shapes for arms 24 are contemplated. For example, arms 24 may include portions which are flat, triangular, chamfered, etc. Additionally, arms 24 may include a variety of surface textures (e.g., smooth, bumpy, etc.), if desired.

Arms 24 of collapsible frame 22 may collectively define a stent containment region 38 opening out to the distal end of collapsible frame 22. Stent containment region 38 may be configured to receive a stent therein during delivery of the stent to a body lumen.

Figure 4:
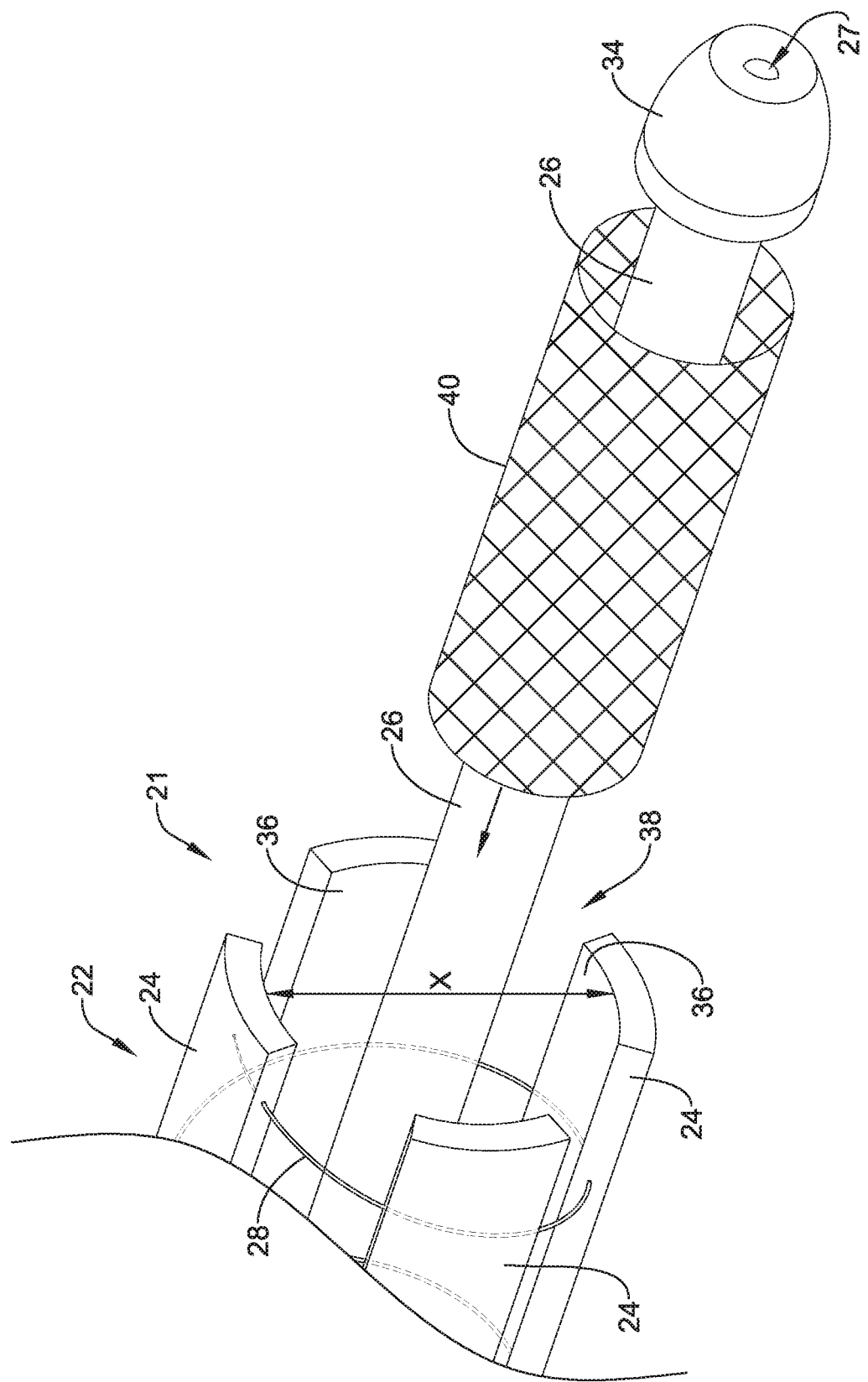
FIGS. 4-6 illustrate aspects of loading a stent into the distal end region of the stent delivery system of FIG. 1.
Figure 5:
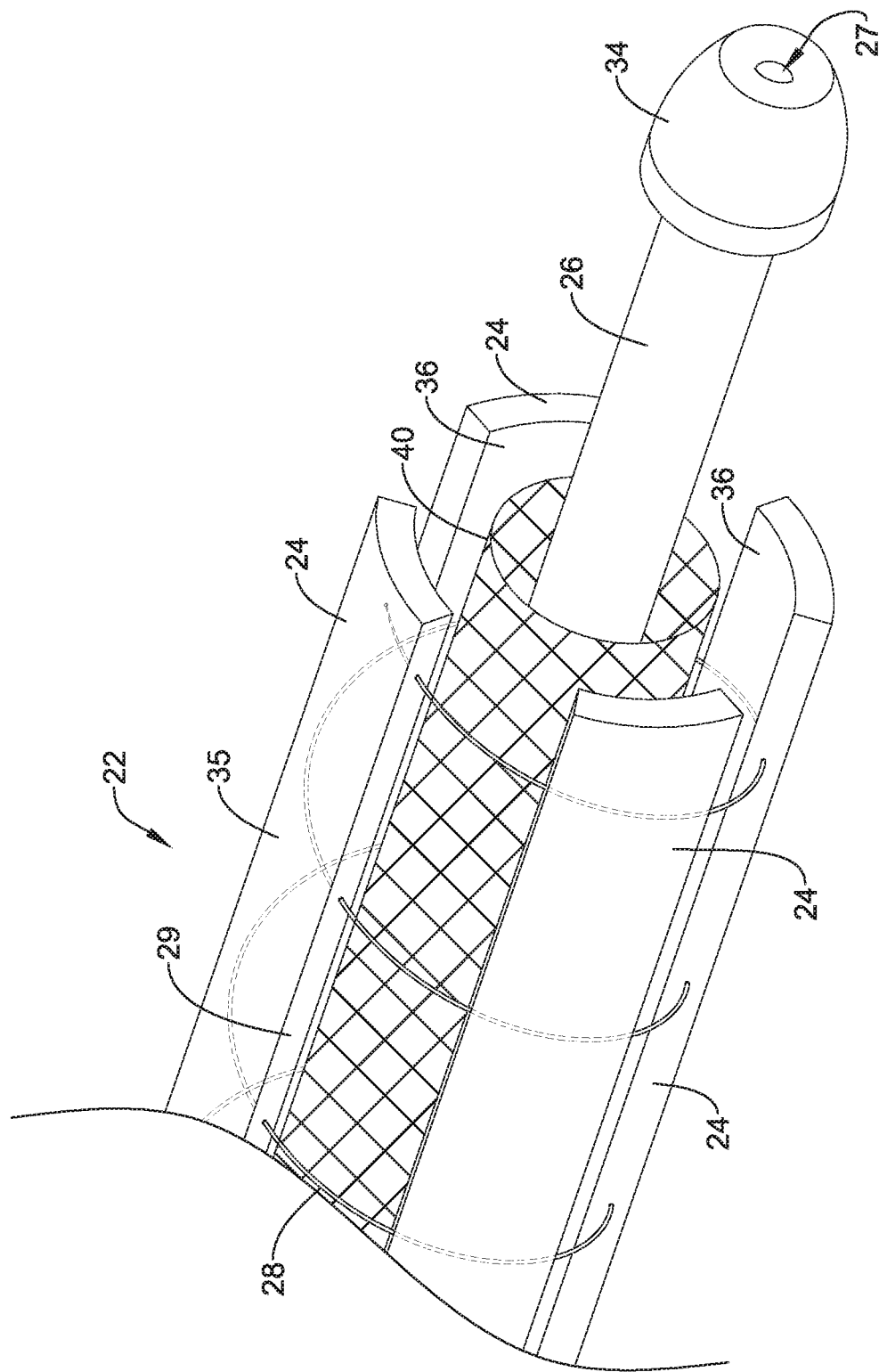
Figure 6:
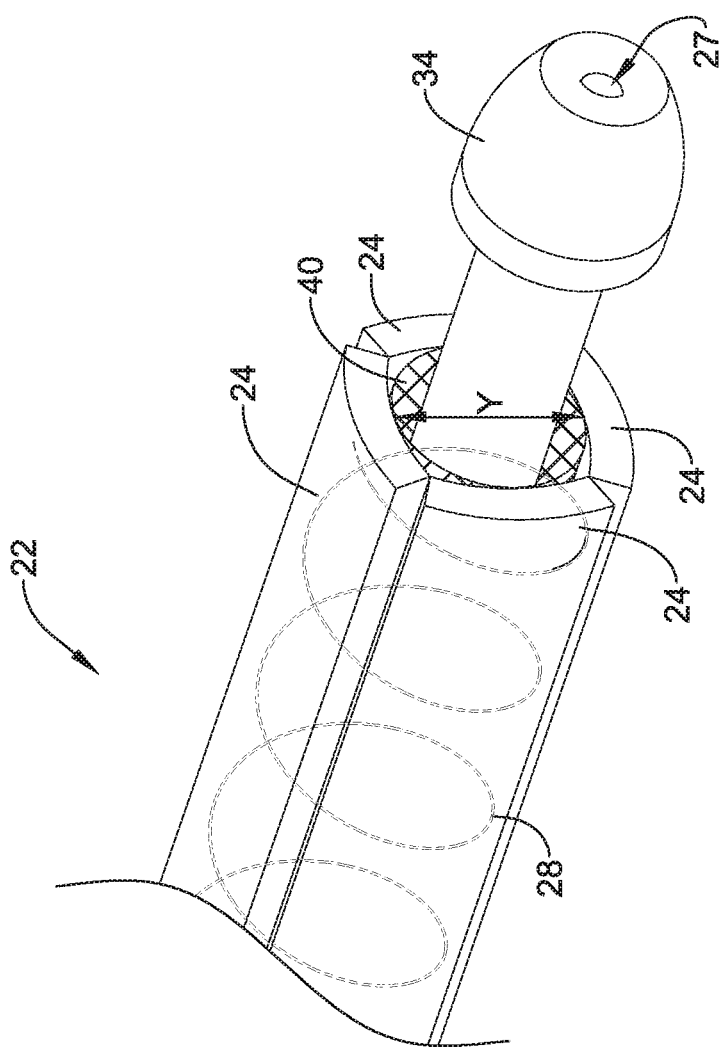

FIGS. 4-6 illustrate aspects of loading a stent 40 into the stent containment region 38 of collapsible frame 22 of the stent delivery system 10. The stent 40 may be a self-expanding stent, having a natural, expanded configuration (e.g., unconstrained) having a first diameter. The stent 40 may be radially collapsed to a constrained configuration having a second diameter less than the first diameter for delivery into a body lumen or cavity. Once deployed from the stent delivery system 10, the stent 40 may automatically expand back toward its natural, expanded configuration when unconstrained by the stent delivery system 10.

It should be noted that, for illustration purposes, inner member 26 is not shown in FIGS. 4-6. However, it is contemplated that inner member 26 may extend through the lumen of stent 40, stent containment region 38 and/or expandable frame 22 shown in FIGS. 4-6 in a manner consistent with that described above with respect to FIGS. 1-2. In other words, it is contemplated that inner member 26 may extend through both expandable fame 22 and/or stent 40, whereby a distal end of inner member 26 may be positioned distally of expandable frame 22 and/or stent 40. Further, as described above, inner member 26 may include one or more features (e.g., holder, markers, etc.) that aid in the positioning, alignment and/or loading of stent member 40 onto inner member 26 and/or within stent containment region 38. FIGS. 4 and 5 illustrate an example stent 40 being positioned within stent containment region 38 defined by arms 24 of collapsible frame 22. Stent 40 may be loaded into the stent containment region 38 with the stent 40 in its natural, expanded size and configuration. As depicted by the arrow shown in FIG. 4, stent 40 may be positioned (e.g., loaded) into the distal end 21 of collapsible frame 22 with collapsible frame 22 in an expanded configuration. Stent containment region 38 may have a diameter X in the expanded configuration, shown in FIG. 4, corresponding to the distance across a circle inscribed within the arms 24 of collapsible frame 22. It can be appreciated that to facilitate loading of stent 40, the diameter X of stent containment region 38 in the expanded configuration may be larger than the outer diameter of stent 40.

FIG. 5 shows stent 40 after being positioned within stent containment region 38 (discussed with respect to FIG. 4 above) with collapsible frame 22 still in the expanded configuration. As shown in FIG. 5, a distal end of stent 40 may be substantially flush with the distal end 21 of collapsible frame 22. Alternatively, the distal end of stent 40 may be located proximal of the distal end 21 of collapsible frame 22, or the distal end of stent 40 may extend slightly distal of the distal end 21 of collapsible frame 22, if desired. Additionally, it can be appreciated that the arrangement of arms 24 in the expanded configuration may substantially surround stent 40.

As discussed above, collapsible frame 22 may then be actuated to collapse stent 40 around inner member 26 within collapsible frame 22. The process of inserting stent 40 into stent containment region 38, followed by collapsing stent 40 may generally be defined as "loading" the stent 40 into stent delivery system 10. It can be appreciated that collapsing stent 40 may require arms 24 to shift radially inward while surround stent 40. In other words, arms 24 may collectively collapse radially inward on stent 40.

Actuation member 28 may be actuated (e.g., pulled proximally) to radially collapse arms 24 around stent 40. It can be appreciated that actuating the actuation member 28 may uniformly collapse arms 24 radially inward upon stent 40. For example, as discussed with respect to FIG. 1, actuation member 28 may extend from collapsible frame 22 to handle member 30. Further, actuation member 28 may be attached to actuator 32 (e.g., wheel member, lever, cam, knob, etc.). Actuator 32 may be actuated (e.g., rotated) such that actuation member 28 is retracted (e.g., pulled) in a proximal direction through a lumen in shaft 16 (discussed above). As actuation member 28 is retracted proximally, actuation member 28 slides through openings of arms 24 and thereby forces arms 24 radially inward. For example, actuation member 28 cinches down around arms 24 to collapse arms 24 to the collapsed configuration. The movement of arms 24 radially inward effectively tightens arms 24 around stent 40, thereby shifting the collapsible frame 22 into a collapsed configuration. Arms 24 apply a radially inward force against stent 10 to collapse stent 40 from its natural, expanded configuration to a reduced diameter collapsed or constrained configuration.

FIG. 6 illustrates stent member 40 in a collapsed configuration. As shown in FIG. 6, the inner surfaces 36 (shown in FIG. 5) of arms 24 have been radially collapsed around the outer surface of stent 40. Further, FIG. 6 shows the diameter Y of stent containment region 38 in a collapsed configuration, corresponding to the distance across a circle inscribed within the arms 24 of collapsible frame 22. It can be appreciated that diameter Y may be less than diameter X of FIG. 4. The configuration of stent 40 shown in FIG. 6 may be defined as a "loaded" or "pre-deployment" configuration of stent 40 within stent delivery system 10. In this configuration stent 40 may be constrained to a smaller diameter to facilitate delivery to a body lumen or cavity.

While not shown in the figures, it can be appreciated that handle member 30 may include a locking mechanism that prohibits actuation member 28 from being inadvertently released once stent member 40 has been positioned in a loaded configuration as described in FIG. 6. It is also contemplated that a locking mechanism included in handle 30 may be selectively released by a clinician at a desired point in a medical procedure. Upon releasing the locking mechanism, arms 24 may be permitted to radially expand (e.g., expand due to an outward force placed upon them by stent 40).

Figure 7:
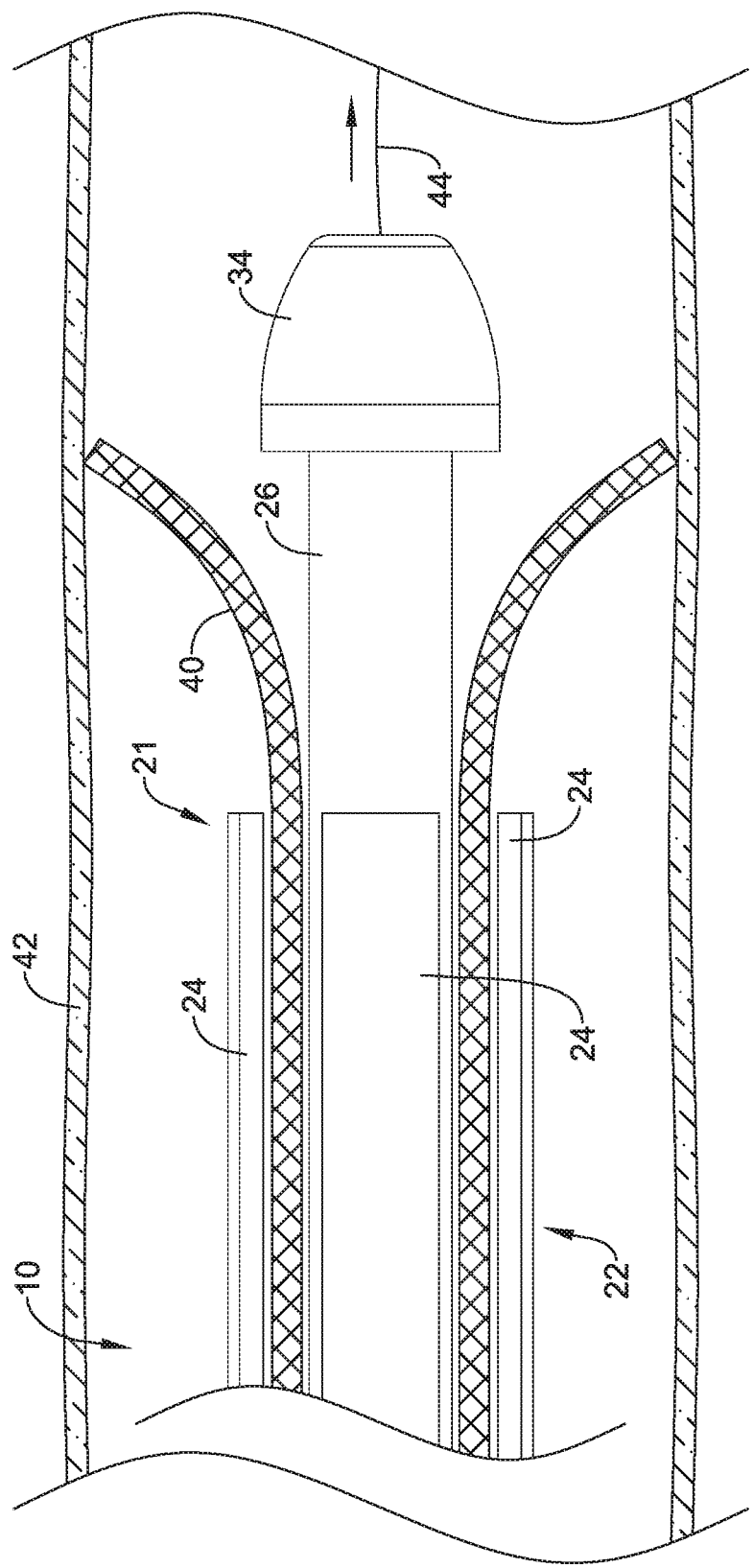
FIG. 7 illustrates aspects of deploying a stent from the stent delivery system in a body lumen.

FIG. 7 shows stent delivery system 10 positioned inside a body lumen 42. As described above, the stent delivery system shown in FIG. 7 may be advanced through body lumen 42 along guidewire 44, for example. Further, FIG. 7 shows stent 40 being advanced (e.g., deployed) from the distal end 21 of collapsible frame 22. In some examples, stent 40 may be advanced out of the distal end 21 of collapsible frame 22 by moving inner member 26 distally relative to shaft 16 and collapsible frame 22 and/or moving collapsible frame 22 and shaft 16 proximally relative to stent 40 and inner member 26. For example, a clinician may be able to advance inner member 26 (from outside the body, as described above) relative to collapsible frame 22. Further, inner member 26 may include a portion along its outer surface that interfaces with stent 40. Therefore, it can be appreciated that the advancement of inner member 40 may expel stent 40 out of the distal end 21 of collapsible frame 22. The arrow in FIG. 7 depicts inner member 26 being advanced in a distal direction. Further, FIG. 7 shows the distal portion of stent 40 being released out the distal end 21 of collapsible frame 22. As stent 40 is expelled from collapsible frame 22, stent 40 may automatically expand radially outward to engage a luminal surface of body lumen 42.

Figure 8:
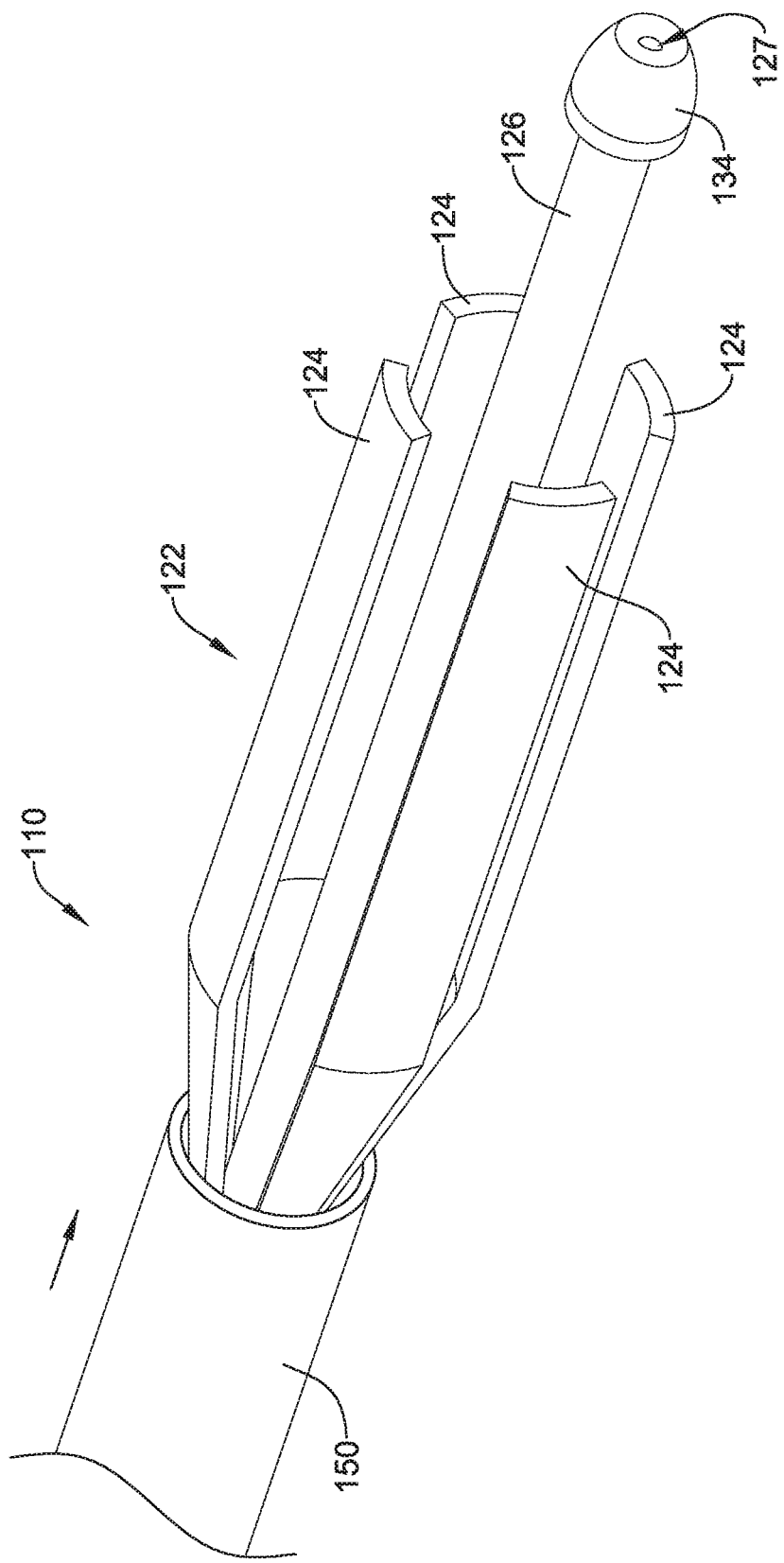
FIG. 8 illustrates another example stent delivery system having a stent containment region in an expanded configuration.
Figure 9:
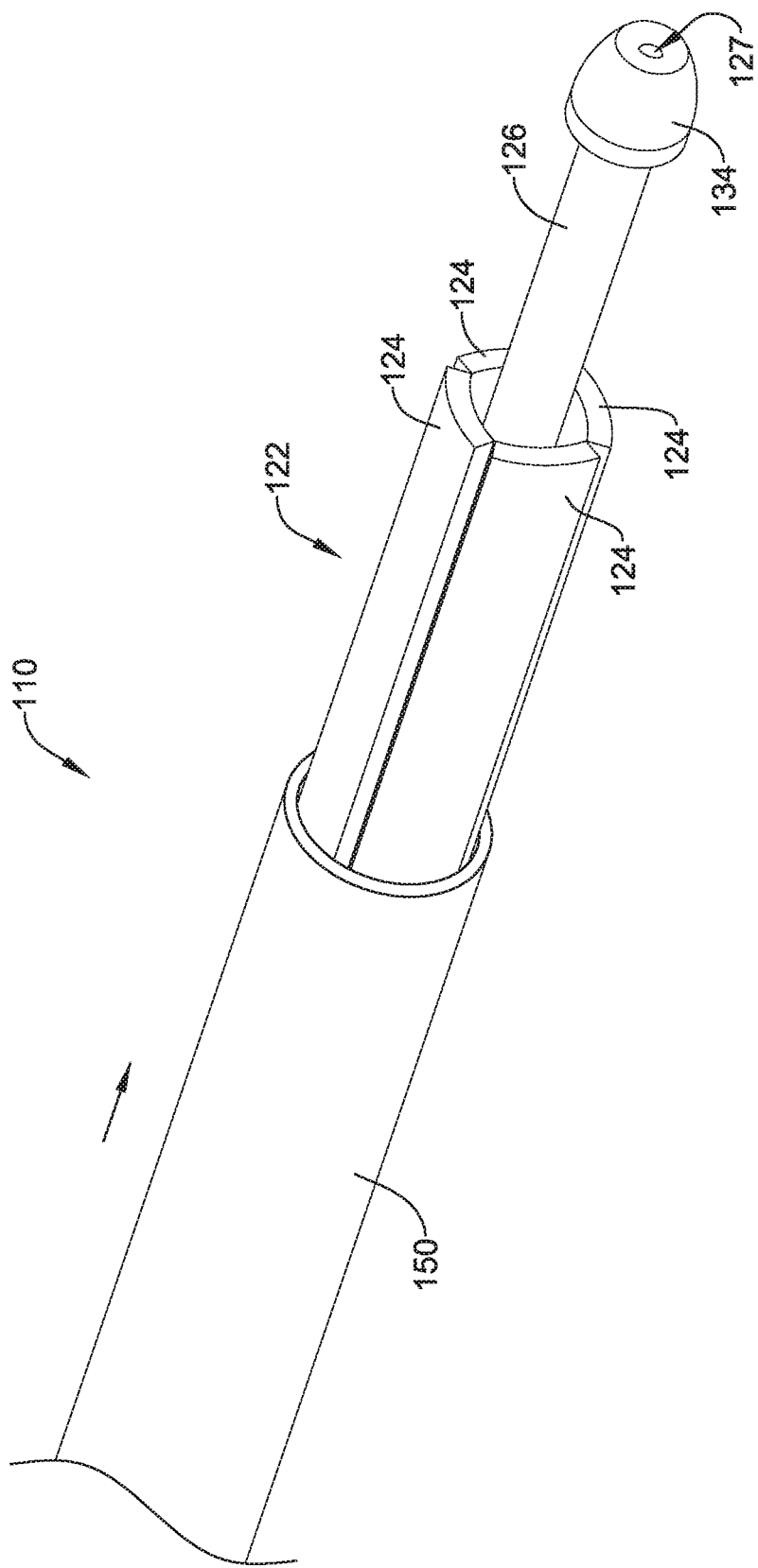
FIG. 9 illustrates the stent delivery system of FIG. 8 having the stent containment region in a collapsed configuration.

FIGS. 8 and 9 illustrate another example stent delivery system 110. Stent deliver system 110 shown in FIG. 8 includes a collapsible frame 122 having arms 124. Additionally, stent delivery system 122 may include inner member 126 having tip member 134 and guidewire lumen 127. It can be appreciated from the following examples that the collapsible frame collapsible frame 122, arms 124 and inner member 126 are similar both in structure and operation as that described above with respect to FIGS. 1-7.

However, FIG. 8 further illustrates outer sheath member 150. Outer sheath member may be positioned over an example shaft (not shown in FIG. 8, but similar to shaft 16 described above). Outer sheath member 150 may slide, translate, advance, etc. with respect to collapsible frame 122 (including arms 124). Additionally, outer sheath member 150 may be able to be advanced distally over collapsible frame 122. For example, as depicted by the arrow in FIG. 8, outer sheath member 150 may translate in a distal direction toward the distal end of collapsible frame 122. Further, outer sheath member 150 may include an inner diameter which, when outer sheath member 150 is advanced distally, forces arms 124 radially inward. The distal advancement of outer sheath member 150 may force arms 124 to tighten (e.g., collapse) around an example stent.

FIG. 9 shows collapsible frame 122 in a collapsed configuration with outer sheath member 150 advanced in a distal direction along at least a portion of arms 124 to surround arms 124. It can be appreciated from FIG. 9 that the inner surface of outer sheath 150 is contacting the outer surfaces of arms 124, thereby radially collapsing arms 124 inward. While a stent is not shown in FIG. 8 or 9, it can be appreciated that the example stent system 10 described relative to FIGS. 8 and 9 may collapse a self-expandable stent from an unconstrained configuration to a collapsed configuration similar to the stent delivery system described with respect to FIGS. 1-7 above.

The example stent delivery systems described herein may be utilized to load and deliver stents, such as self-expandable stents, having a variety of shapes and configurations. Further, the stent delivery systems described herein may be particularly advantageous to load and deliver large diameter stents. An example methodology for loading an example stent may include initially expanding the arms of the collapsible frame to a diameter sufficiently large to advance a desired stent therein with the stent in its natural, expanded configuration (e.g., unconstrained, expanded configuration). Expanding the arms to a sufficient diameter may create a stent containment region as described above large enough to receive the stent therein. The stent may then be positioned inside the stent containment region and appropriately aligned along an inner member with the stent surrounding the inner member. The inner member may include markings and/or other positioning aids to facilitate proper stent placement. The collapsible frame is then collapsed around the stent using one or more of the examples disclosed herein (e.g., retracting a pull wire, distal advancement of an outer sheath, etc.) to collapse the stent to a collapsed or constrained diameter for delivery. The collapsible frame may then be locked in a collapsed configuration prior to insertion into the patient and advancement to the target site. Once positioned at the target site, the stent may then be deployed from the collapsible frame (via distal advancement of the inner member, for example). The stent may be deployed out of the distal end of the collapsible frame while the collapsible frame is maintained in a collapsed configuration. The stent may automatically expanded radially outward as the stent is expelled from the collapsible frame.

Any of the examples described herein may include one or more markers designed to assist a clinician in locating, positioning and/or advancing stent delivery system 10/110 within a patient or relative to other structures (e.g., other medical devices). Further, any of the components (e.g., pull wire, inner member, arms, etc.) of stent delivery system 10/110 may include a marker (e.g., radiopaque marker) which may assist in loading the stent with the delivery system 10/110 and/or visualizing the advancement of or proper placement of the stent member within a patient.

The materials that can be used for the various components of stent delivery system 10/110 (and components thereof) disclosed herein may include those commonly associated with medical devices. For simplicity purposes, the following discussion makes reference to stent delivery system 10/110 (and components thereof). However, this is not intended to limit the devices and methods described herein, as the discussion may be applied to other similar stent delivery systems or devices disclosed herein.

Stent delivery system 10/110 (and components thereof) may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of stent delivery system 10/110 (and components thereof) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent delivery system 10/110 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of stent delivery system 10/110 (and components thereof) to achieve the same result.

In some embodiments, a degree of Magnetic Resonance Imaging (Mill) compatibility is imparted into stent delivery system 10/110. For example, stent delivery system 10/110 (and components thereof), or portions thereof, may be made of a material that does not substantially distort the image and create substantial artifacts (e.g., gaps in the image). Certain ferromagnetic materials, for example, may not be suitable because they may create artifacts in an MRI image. Stent delivery system 10/110 (and components thereof), or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A stent delivery device, comprising:
an elongate shaft including a proximal region, a distal region and at least one lumen extending therein;
a collapsible frame attached to the distal region of the elongate shaft, the collapsible frame including a plurality of arms configured to surround a stent such that the plurality of arms define a stent containment region;
an inner member extending through the stent containment region such that a distal tip of the inner member is positionable distal of a stent when contained therein; and
a pull wire configured to actuate the plurality of arms of the collapsible frame from an expanded configuration to a collapsed configuration;
wherein each of the plurality of arms includes a plurality of openings formed therein, the plurality of openings being longitudinally spaced apart along their respective arm;
wherein at least a portion of the pull wire extends helically around the inner member and through more than one of the plurality of openings formed in each arm of the plurality of arms.

2. The stent delivery device of claim 1, wherein the pull wire extends around the inner member in a substantially continuous configuration.

3. The stent delivery device of claim 1, wherein the collapsible frame further includes at least one aperture defined between one or more of the plurality of arms, wherein the aperture has a width, and wherein the aperture width decreases as the pull wire is actuated.

4. The stent delivery device of claim 1, wherein each of the plurality of arms includes a distal portion and a proximal portion, wherein each of the proximal portions includes a flexible region positioned distal to a distal end of the elongate shaft.

5. The stent delivery device of claim 4, wherein each of the flexible regions includes a flexible joint configured to maintain a substantially constant distance between the distal portion of its respective arm and the elongate shaft.

6. The stent delivery device of claim 1, further comprising a stent disposed within the stent containment region, wherein each of the plurality of arms extends an entire length of the stent.

7. The stent delivery device of claim 6, wherein the stent is positioned between an inner surface of each of the plurality of arms and an outer surface of the inner member.

8. The stent delivery device of claim 7, wherein the inner surface of each of the plurality of arms defines a concave surface with respect to the outer surface of the inner member, and wherein each of the concave surfaces are configured to mate with an outer surface of the stent.

9. The stent delivery device of claim 6, wherein the plurality of arms is configured to completely encircle the stent disposed within the stent containment region in the collapsed configuration.

10. The stent delivery device of claim 1, wherein the distal tip is configured to abut a distal end of each of the plurality of arms in the collapsed configuration.

11. A stent delivery system, comprising:
an elongate shaft including a proximal region, a distal region and at least one lumen extending therein;
a collapsible frame attached to the distal region of the elongate shaft, the collapsible frame including a plurality of arms, the plurality of arms collectively defining a stent containment region;
an inner member slidably disposed in the lumen of the elongate shaft and extending distally beyond the stent containment region, the inner member including a distal tip, wherein the inner member is configured to extend entirely through a length of a stent disposed within the stent containment region such that the distal tip is positioned distal of the stent when contained therein; and
a pull wire disposed along at least one of the plurality of arms;
wherein the plurality of arms are configured to surround a stent;
wherein the stent containment region has a first diameter corresponding to an expanded configuration and a second diameter corresponding to a collapsed configuration, and wherein actuation of the pull wire is designed to shift the stent containment region from the first diameter to the second diameter;
wherein each of the plurality of arms includes a proximal portion and a distal portion, each of the proximal portions including a flexible region positioned distal to a distal end of the elongate shaft, each of the distal portions extending from the flexible region to a distal end of its respective arm;
wherein the distal portion of each of the plurality of arms is oriented substantially parallel to a longitudinal axis of the elongate shaft in the collapsed configuration and in the expanded configuration;
wherein each of the plurality of arms includes a plurality of passages extending circumferentially therethrough;
wherein at least a portion of the pull wire extends helically around the inner member and through more than one of the plurality of passages extending circumferentially through each arm of the plurality of arms.

12. The stent delivery device of claim 11, wherein the pull wire extends around the inner member in a substantially continuous configuration.

13. The stent delivery device of claim 11, further comprising a stent disposed within the stent containment region.

14. The stent delivery device of claim 11, wherein an inner surface of each of the plurality of arms defines a circumferentially concave surface with respect to an outer surface of the inner member.

15. A stent delivery device, comprising:

a stent;

an elongate shaft including a proximal region, a distal region and at least one lumen extending therein;

a collapsible frame attached to the distal region of the elongate shaft, the collapsible frame including a plurality of arms surrounding the stent such that the plurality of arms define a stent containment region, each of the plurality of arms extending distally beyond a distal end of the stent;

an inner member slidably disposed in the lumen of the elongate shaft, the inner member extending through the stent such that a distal tip of the inner member is positioned distal of the distal end of the stent; and a pull wire configured to actuate the plurality of arms of the collapsible frame from an expanded configuration to a collapsed configuration to radially constrain the stent in the stent containment region such that none of the stent extends outside of the stent containment region in the collapsed configuration;

wherein each of the plurality of arms includes a plurality of openings extending circumferentially therethrough, the plurality of openings being longitudinally spaced apart along their respective arm;

wherein at least a portion of the pull wire extends through each of the plurality of openings extending circumferentially through each arm of the plurality of arms.

16. The stent delivery device of claim 15, wherein the pull wire extends helically around the inner member in a substantially continuous configuration.

17. The stent delivery device of claim 15, wherein in the collapsed configuration, each of the plurality of arms abuts circumferentially adjacent arms and the distal tip abuts a distal end of each of the plurality of arms.

* * * * *